United States Patent
Burton et al.

(10) Patent No.: US 8,192,675 B2
(45) Date of Patent: Jun. 5, 2012

(54) CUTTING BALLOON WITH CONNECTOR AND DILATION ELEMENT

(75) Inventors: David G. Burton, Bloomington, IN (US); Darin G. Schaeffer, Bloomington, IN (US); David A. Drewes, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 427 days.

(21) Appl. No.: 12/399,705

(22) Filed: Mar. 6, 2009

(65) Prior Publication Data
US 2009/0234283 A1 Sep. 17, 2009

Related U.S. Application Data

(60) Provisional application No. 61/036,175, filed on Mar. 13, 2008.

(51) Int. Cl.
*B29C 49/04* (2006.01)
(52) U.S. Cl. ......... 264/515; 264/514; 264/532; 264/541
(58) Field of Classification Search .................. None
See application file for complete search history.

(56) References Cited

U.S. PATENT DOCUMENTS

| | | | |
|---|---|---|---|
| 4,535,757 A | 8/1985 | Webster, Jr. | |
| 4,729,763 A | 3/1988 | Henrie | |
| 4,877,030 A | 10/1989 | Beck et al. | |
| 4,886,061 A | 12/1989 | Fischell et al. | |
| 4,898,575 A | 2/1990 | Fischell et al. | |
| 4,983,167 A | 1/1991 | Sahota | |
| 5,009,659 A | 4/1991 | Hamlin et al. | |
| 5,019,042 A | 5/1991 | Sahota | |
| 5,030,201 A | 7/1991 | Palestrant | |
| 5,047,040 A | 9/1991 | Simpson et al. | |
| 5,057,120 A | 10/1991 | Farcot | |
| 5,078,723 A | 1/1992 | Dance et al. | |
| 5,080,660 A | 1/1992 | Buelna | |
| 5,090,958 A | 2/1992 | Sahota | |
| 5,112,305 A | 5/1992 | Barath et al. | |
| 5,147,377 A | 9/1992 | Sahota | |
| 5,160,321 A | 11/1992 | Sahota | |
| 5,181,920 A | 1/1993 | Mueller et al. | |

(Continued)

FOREIGN PATENT DOCUMENTS

WO WO0160443 A 8/2001

(Continued)

OTHER PUBLICATIONS

International Search Report issued by the PCT in related Patent Application PCT/US2009/036361 filed Mar. 6, 2009.

*Primary Examiner* — Monica A Huson
(74) *Attorney, Agent, or Firm* — Brinks Hofer Gilson Lione

(57) ABSTRACT

A balloon catheter is provided that may be used to dilate hardened regions of a stenosis. The balloon catheter is provided with one or more dilation elements that extend along a surface of a balloon. Each dilation element is connected to an outer surface of the balloon by a connector. The connector is sufficiently sized and designed to undergo stress-induced plastic deformation incurred during blow molding so that a significant portion of each of the dilation elements does not become absorbed into the wall of the final blow molded balloon, thereby maintaining the structural integrity of each of the dilation elements.

7 Claims, 12 Drawing Sheets

U.S. PATENT DOCUMENTS

| | | | |
|---|---|---|---|
| 5,192,291 A | 3/1993 | Pannek, Jr. |
| 5,196,024 A | 3/1993 | Barath |
| 5,209,749 A | 5/1993 | Buelna |
| 5,224,945 A | 7/1993 | Pannek, Jr. |
| 5,224,949 A | 7/1993 | Gomringer et al. |
| 5,226,887 A | 7/1993 | Farr et al. |
| 5,320,605 A | 6/1994 | Sahota |
| 5,320,634 A | 6/1994 | Vigil et al. |
| 5,336,178 A | 8/1994 | Kaplan et al. |
| 5,336,234 A | 8/1994 | Vigil et al. |
| 5,342,301 A | 8/1994 | Saab |
| 5,372,601 A | 12/1994 | Lary |
| 5,395,332 A | 3/1995 | Ressemann et al. |
| 5,409,454 A | 4/1995 | Fischell et al. |
| 5,411,478 A | 5/1995 | Stillabower |
| 5,431,673 A | 7/1995 | Summers et al. |
| 5,441,510 A | 8/1995 | Simpson et al. |
| 5,450,843 A | 9/1995 | Moll et al. |
| 5,505,725 A | 4/1996 | Samson |
| 5,522,790 A | 6/1996 | Moll et al. |
| 5,533,968 A | 7/1996 | Muni |
| 5,556,408 A | 9/1996 | Farhat |
| 5,569,277 A | 10/1996 | Evans et al. |
| 5,571,087 A | 11/1996 | Ressemann et al. |
| 5,575,771 A | 11/1996 | Walinsky |
| 5,601,582 A | 2/1997 | Shelton et al. |
| 5,609,574 A | 3/1997 | Kaplan et al. |
| 5,609,628 A | 3/1997 | Keranen |
| 5,616,149 A | 4/1997 | Barath |
| 5,624,704 A | 4/1997 | Darouiche et al. |
| 5,628,746 A | 5/1997 | Clayman |
| 5,690,642 A | 11/1997 | Osborne et al. |
| 5,720,726 A | 2/1998 | Marcadis et al. |
| 5,722,949 A | 3/1998 | Sanese |
| 5,722,979 A | 3/1998 | Kusleika |
| 5,728,129 A | 3/1998 | Summers |
| 5,766,203 A | 6/1998 | Imran et al. |
| 5,779,698 A | 7/1998 | Clayman et al. |
| 5,792,158 A | 8/1998 | Lary |
| 5,797,935 A | 8/1998 | Barath |
| 5,814,061 A | 9/1998 | Osborne et al. |
| 5,904,679 A | 5/1999 | Clayman |
| 5,910,144 A | 6/1999 | Hayashi |
| 5,921,958 A | 7/1999 | Ressemann et al. |
| 5,941,869 A | 8/1999 | Patterson et al. |
| 6,033,380 A | 3/2000 | Butaric et al. |
| 6,036,689 A | 3/2000 | Tu et al. |
| 6,036,708 A | 3/2000 | Sciver |
| 6,071,285 A | 6/2000 | Lashinski et al. |
| 6,123,718 A | 9/2000 | Tu et al. |
| 6,129,706 A | 10/2000 | Janacek |
| 6,165,187 A | 12/2000 | Reger |
| 6,231,572 B1 | 5/2001 | Hart et al. |
| 6,245,040 B1 | 6/2001 | Inderbitzen et al. |
| 6,254,608 B1 | 7/2001 | Solar |
| 6,258,099 B1 | 7/2001 | Mareiro et al. |
| 6,280,464 B1 | 8/2001 | Hayashi |
| 6,283,947 B1 | 9/2001 | Mirzaee |
| 6,306,151 B1 | 10/2001 | Lary |
| 6,355,013 B1 | 3/2002 | van Muiden |
| 6,371,961 B1 | 4/2002 | Osborne et al. |
| 6,500,186 B2 | 12/2002 | Lafontaine et al. |
| 6,508,824 B1 | 1/2003 | Flaherty et al. |
| 6,629,953 B1 | 10/2003 | Boyd |
| 6,632,231 B2 | 10/2003 | Radish, Jr. |
| 6,730,105 B2 | 5/2004 | Shiber |
| 6,746,463 B1 | 6/2004 | Schwartz |
| 6,747,463 B2 | 6/2004 | Rynhart et al. |
| 6,808,531 B2 | 10/2004 | Lafontaine et al. |
| 6,855,124 B1 | 2/2005 | Gonzalez et al. |
| 6,863,856 B1 | 3/2005 | Mahoney et al. |
| 6,942,680 B2 | 9/2005 | Grayzel et al. |
| 6,966,889 B2 | 11/2005 | Saab |
| 7,004,963 B2 | 2/2006 | Wang et al. |
| 7,008,438 B2 | 3/2006 | O'Brien |
| 7,186,237 B2 | 3/2007 | Meyer et al. |
| 7,270,673 B2 | 9/2007 | Yee et al. |
| 7,279,002 B2 | 10/2007 | Shaw et al. |
| 7,291,158 B2 | 11/2007 | Crow et al. |
| 7,303,572 B2 | 12/2007 | Melsheimer et al. |
| 7,314,364 B2 | 1/2008 | Mahoney et al. |
| 7,338,463 B2 | 3/2008 | Vigil |
| 7,354,419 B2 | 4/2008 | Davies et al. |
| 2001/0051810 A1 | 12/2001 | Dubrul et al. |
| 2002/0010489 A1 | 1/2002 | Grayzel |
| 2003/0028212 A1 | 2/2003 | Saab |
| 2003/0040754 A1 | 2/2003 | Mitchell et al. |
| 2003/0040770 A1 | 2/2003 | Radisch, Jr. |
| 2003/0114868 A1 | 6/2003 | Fischell et al. |
| 2003/0114877 A1 | 6/2003 | Gellman |
| 2003/0144677 A1 | 7/2003 | Lary |
| 2003/0153870 A1 | 8/2003 | Meyer et al. |
| 2003/0163148 A1 | 8/2003 | Wang et al. |
| 2003/0229370 A1 | 12/2003 | Miller |
| 2004/0073297 A1 | 4/2004 | Rohde et al. |
| 2004/0111108 A1 | 6/2004 | Farnan |
| 2004/0122457 A1 | 6/2004 | Weber |
| 2004/0122465 A1 | 6/2004 | McMurtry et al. |
| 2004/0127920 A1 | 7/2004 | Radisch |
| 2004/0133223 A1 | 7/2004 | Weber |
| 2004/0143287 A1 | 7/2004 | Konstantino et al. |
| 2004/0193196 A1 | 9/2004 | Appling et al. |
| 2004/0199191 A1 | 10/2004 | Schwartz |
| 2004/0230178 A1 | 11/2004 | Wu |
| 2004/0243156 A1 | 12/2004 | Wu et al. |
| 2004/0243158 A1 | 12/2004 | Konstantino et al. |
| 2005/0021070 A1 | 1/2005 | Feld et al. |
| 2005/0021071 A1 | 1/2005 | Konstantino et al. |
| 2005/0033334 A1 | 2/2005 | Santra et al. |
| 2005/0038383 A1 | 2/2005 | Kelley et al. |
| 2005/0080478 A1 | 4/2005 | Barongan |
| 2005/0090845 A1 | 4/2005 | Boyd |
| 2005/0090846 A1 | 4/2005 | Pedersen et al. |
| 2005/0240148 A1 | 10/2005 | Cheves et al. |
| 2005/0288629 A1 | 12/2005 | Kunis |
| 2006/0015133 A1* | 1/2006 | Grayzel et al. ............ 606/192 |
| 2006/0111736 A1 | 5/2006 | Kelley |
| 2006/0149308 A1 | 7/2006 | Melsheimer et al. |
| 2006/0173487 A1 | 8/2006 | Uflacker et al. |
| 2006/0178685 A1 | 8/2006 | Melsheimer |
| 2007/0073329 A1 | 3/2007 | Hardert |
| 2007/0106215 A1 | 5/2007 | Olsen et al. |
| 2007/0112370 A1 | 5/2007 | Andrews et al. |
| 2007/0142771 A1 | 6/2007 | Durcan |

FOREIGN PATENT DOCUMENTS

WO    WO2004/060460 A    7/2004

* cited by examiner

CUTTING BALLOON WITH CONNECTOR AND DILATION ELEMENT

RELATED APPLICATIONS

This application claims the benefit of priority from U.S. Provisional Application No. 61/036,175, filed Mar. 13, 2008, which is incorporated herein by reference.

BACKGROUND

The present invention relates generally to medical devices and more particularly to balloon catheters used to dilate narrowed portions of a lumen.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. Although the inventions described below may be useful in treating hardened regions of stenosis, the claimed inventions may also solve other problems as well.

SUMMARY

The invention may include any of the following aspects in various combinations and may also include any other aspect described below in the written description or in the attached drawings.

In a first aspect, a method of forming a balloon is provided. A blow mold parison is provided comprising a substantially cylindrical body portion, the body portion comprising an outer wall and an inner wall, the body portion further comprising an aperture extending along a central axis of the body portion; an extension element projecting away from the outer wall, the extension element comprising a first height and a first effective width; and a structural feature projecting away from the outer wall of the body portion, the structural feature being integrally molded to the extension element, the structural feature comprising a second effective width greater than the first effective width of the extension element. The blow parison is inserted into a forming mold. A predetermined amount of heat and pressure is applied to the parison. The parison is stretched in a longitudinal direction. The parison is expanded in a radial direction, wherein the extension element undergoes stress-induced plastic deformation developed during the radial expansion to maintain the structural integrity of the structural feature.

In a second aspect, a balloon catheter for dilation of a vessel wall is provided. The balloon catheter comprises a balloon having a distal portion, and a proximal portion, wherein at least a length of an outer surface of the balloon comprises a working diameter adapted to dilate the vessel wall; a shaft having a distal end and a proximal end, the balloon being mounted on the distal end of the shaft, wherein the shaft further comprises an inflation lumen extending therethrough in fluid communication with an interior region of the balloon, the balloon thereby being expandable between a deflated state and an inflated state; and a protuberance disposed along the outer surface of the balloon, the protuberance being affixed to the outer surface of the balloon at an interface region, the protuberance comprising a dilation element and a connector, the dilation element extending away from the outer surface of the balloon and being characterized by a second effective width, the connector connecting the dilation element to the outer surface of the balloon at the interface, the connector characterized by a first effective width less than the second effective width of the protrusion.

In a third aspect, a blow mold parison for a balloon is provided. The parison comprises a substantially cylindrical body portion, the body portion comprising an outer wall and an inner wall, the body portion further comprising an aperture extending along a central axis of the body portion; an extension element extending from the outer wall of the body portion, the extension element projecting away from the outer wall, the extension element comprising a first height and a first effective width; and a structural feature projecting from the outer wall of the body portion, the structural feature being integrally molded to the extension element, the structural feature comprising a second effective width greater than the first effective width of the extension element.

BRIEF DESCRIPTION OF SEVERAL VIEWS OF THE DRAWINGS

The invention may be more fully understood by reading the following description in conjunction with the drawings, in which.

DETAILED DESCRIPTION

As used herein, the term "extension element" refers to a slender portion that connects a structural feature to the outer wall of a parison. The "extension element" becomes a "connector" of a balloon after a blow molding process. The term "structural feature" refers to that portion of the parison that becomes a "dilation element" of the balloon after the blow molding process.

Figure 1:
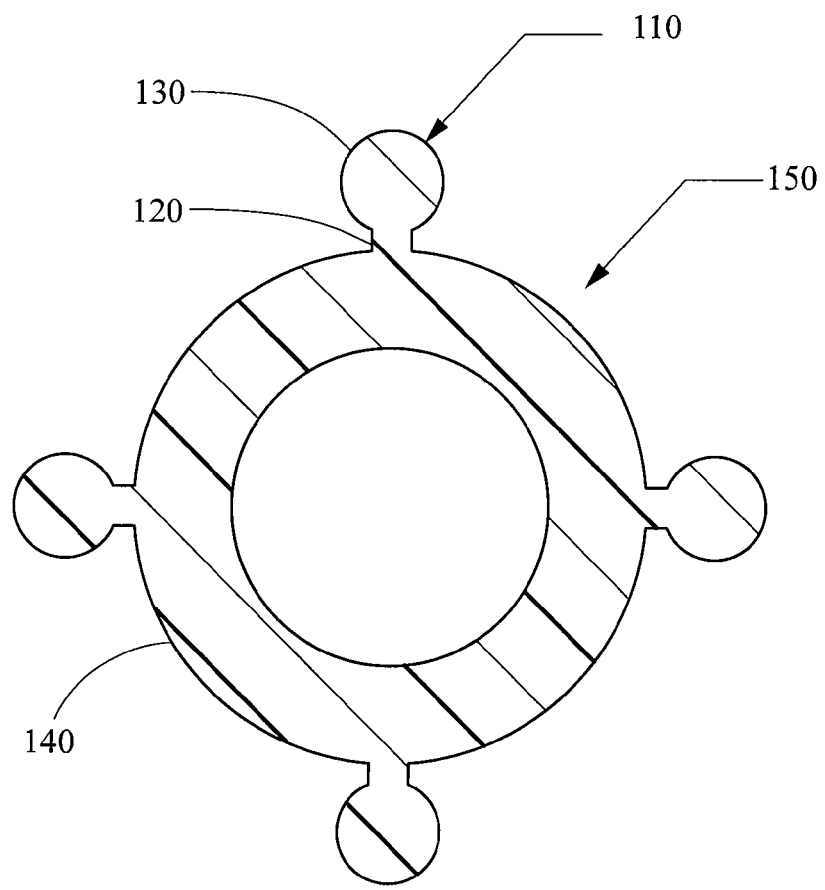
FIG. 1 is a cross-sectional view of a balloon including a dilation element connected to an outer surface of the balloon by a connector.

FIG. 1 shows a cross-sectional view of a balloon 150 comprising a preferred design configuration of protuberances 110 disposed along an outer surface 140 of the balloon 150. The protuberances 110 are shown to be integral with the outer surface 140 of the balloon 150. Each of the protuberances 110 comprises a dilation element 130 and a connector 120. The connector 120 is preferably integrated into the outer surface 140 of the balloon 150. During the blow molding process used to form the balloon 150, the connector 120 is sufficiently sized such that a portion of the connector or all of the connector 120 is absorbed into the wall of the balloon 150 to maintain the structural integrity of the dilation element 130, as will be explained in detail below. During inflation of the balloon 150, the force exerted by the inflated balloon 150 may be focused to the dilation elements 130 and thereafter transferred through the dilation elements 130 to a stenosed vessel wall. The concentrated force exerted by the dilation elements 130 against the stenosed region is sufficient to fracture plaque from the vessel wall.

Figure 2:
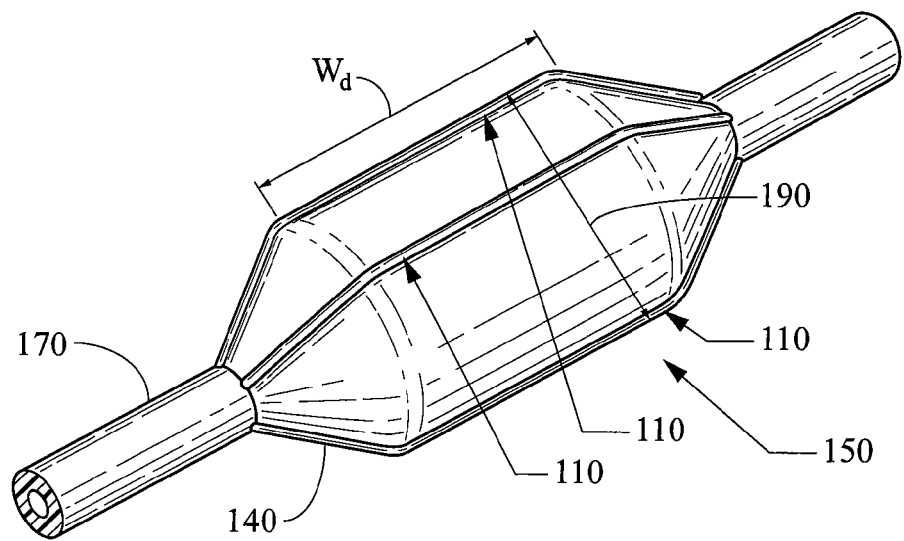
FIG. 2 shows a perspective view of the balloon of FIG. 1 with the balloon mounted on a shaft.

FIG. 2 shows the balloon 150 connected to a shaft 170. The outer surface 140 of the balloon 150 has a working diameter 190 that extends along part of the length of the balloon 150. The length Wd of the working diameter may be defined as the distance between the balloon proximal end, where the tapered proximal portion meets the working diameter 190 and the balloon distal end, where the tapered distal portion meets the working diameter 190. The working diameter 190 of the balloon 150 may be connected to the shaft 170 with the tapered proximal portion and the tapered distal portion of the balloon 150. Typically, the working diameter 190 of the balloon 150 is a portion that inflates to a generally uniform circumference in order to evenly dilate a section of a lumen. However, the working diameter 190 does not necessarily need to have a uniform circumference.

Still referring to FIG. 2, the protuberances 110 are shown to continuously extend in the longitudinal direction along the working diameter 190 of the balloon 150 and the tapered proximal and distal portions of the balloon 150. The protuberances 110 are oriented about a circumference of the outer surface 140 of the balloon 150 and are shown circumferentially spaced apart from each other about the outer surface 140 of the balloon 150. Other configurations of the protuberances 110 about the outer surface 140 of the balloon 150 are contemplated. For example, the protuberances 110 may be configured in a spiral arrangement about the balloon 150 or extend only about the working diameter 190 of the balloon 150.

Alternatively, the protuberances 110 may extend along at least a portion of the proximal neck and/or distal neck of the balloon 150 where the balloon 150 is bonded to the shaft 170. In one embodiment, at least a portion of the protuberances 110 that extend along the neck of the balloon 150 is heat bonded to the shaft 170. In particular, the overall dimensions of the protuberances 110 may gradually increase from the heat bonded region to the working diameter 190 of the balloon 150. Such a transitioning in the bead size may assist with the refolding of the balloon 150 into a pleated configuration (discussed in greater detail below in conjunction with FIG. 19). Additionally, the transitioning may facilitate insertion and withdrawal of the balloon 150 from an outer delivery sheath that is commonly utilized during the angioplasty procedure.

The number of protuberances 110 oriented about the balloon 150 may also vary. The exact number of protuberances 110 is dependent upon a number of factors, including, but not limited to, the type of stenosed region into which the balloon 150 is inserted. In a preferred embodiment, the balloon 150 has three or four protuberances 110, the exact number being dependent to a degree upon the balloon profile that is suitable for a particular application.

Figure 3:
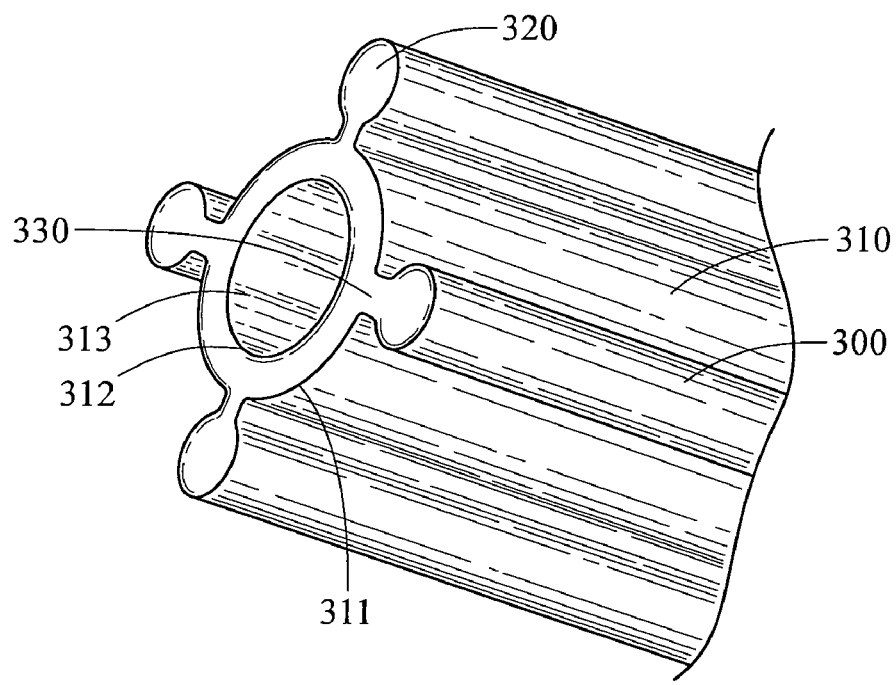
FIG. 3 shows a parison precursor to the final balloon of FIGS. 1 and 2.

Forming the final shape of the balloon 150 typically involves a blow molding process. FIG. 3 shows a parison 300, which is the precursor structure to the final shaped balloon 150 shown in FIGS. 1 and 2. The term "parison" as used herein refers to the raw balloon tubing prior to blow molding the final balloon 150 structure. Generally speaking, blow molding of the parison 300 transforms the parison 300 into the final shaped balloon 150. Preferably, the parison 300 is formed from a screw extrusion process as is known to one of ordinary skill in the art. The parison 300 comprises a cylindrical body portion 310. The body portion 310 includes an outer wall 311 and an inner wall 312. An aperture 313 extends through the central axis of the body portion 310. The aperture 313 becomes the inflation lumen of the balloon 150 after blow molding. The parison 310 further includes a structural feature 320 which projects away from the outer wall 311 of the body portion 310. The structural feature 320 becomes the dilation element 130 after the blow molding process. An extension element 330 connects the structural feature 320 to the outer wall 311 of the body portion 310. The extension element 330 becomes the connector 120 after the blow molding process. The extension element 330 is preferably integrally molded into the outer wall 311 of the body portion 310.

Figure 4:
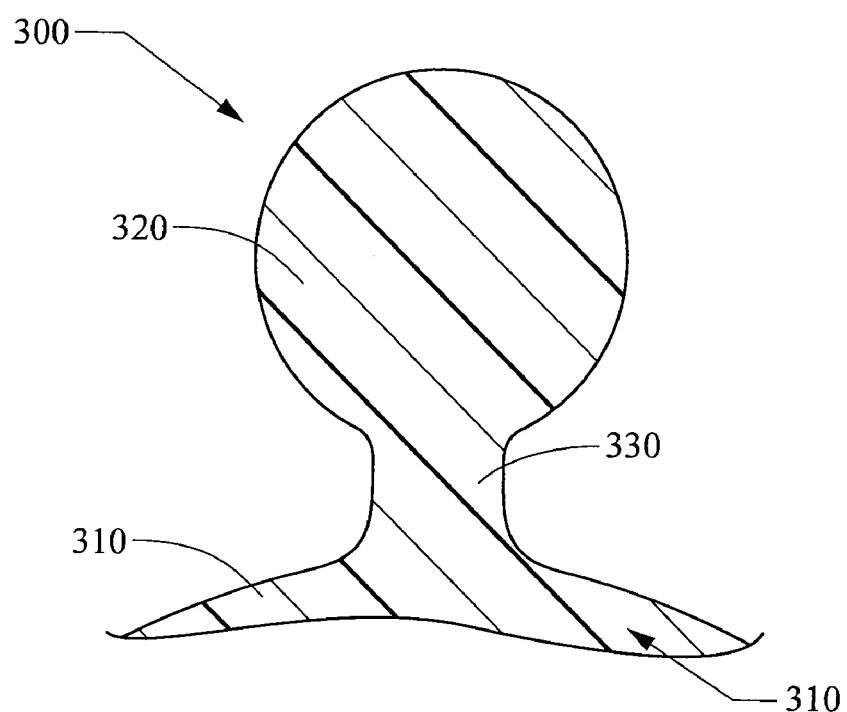
FIG. 4 shows a blown-up cross-sectional view of FIG. 3 and shows the structural feature and extension element integrally molded into the outer wall of the body portion.

FIG. 4 is a blown up cross-sectional view of FIG. 3 and shows the structural feature 320 and extension element 330 integrally molded into the outer wall 311 of the body portion 310. As will be explained, the extension element 330 is designed to prevent significant absorption of the structural feature 320 into the wall of the cylindrical body portion 310 of the parison 300 during the blow molding process, thereby maintaining the structural integrity of the dilation element 130 of the balloon 150.

Figure 5:
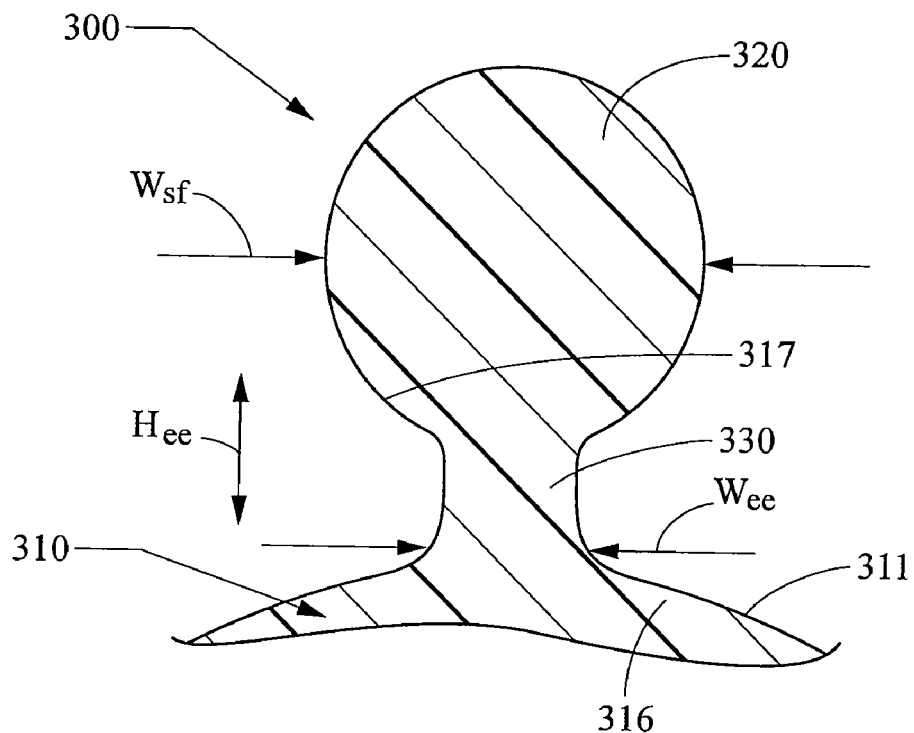
FIG. 5 shows a blown-up cross-sectional view of FIG. 3 in which the parison is unstretched in the longitudinal and radial directions.

FIG. 5 shows another blown up cross-sectional view of FIG. 3. FIG. 5 represents the parison 300 prior to being longitudinally and radially stretched during the blow molding process. Extension element 330 is shown to have a first effective width $W_{ee}$. The first effective width $W_{ee}$ as used herein means the largest lateral dimension of the extension element 330. FIG. 5 indicates that the largest lateral dimension of the extension element 330 is situated close to the outer wall 311 of body portion 310. The largest lateral dimension of the extension element 330 may be situated anywhere else along the extension element 330. The extension element 330 may also be characterized by a height, $H_{ee}$. The height $H_{ee}$ spans from the base 316 of the outer wall 311 to the base 317 of the structural feature 320. The base 316 may be designed with a predetermined radius of curvature to alleviate the stress incurred during blow molding, thereby facilitating absorption of the extension element 330 into the wall of the body portion 310.

FIG. 5 shows that the structural feature 320 has a second effective width, $W_{sf}$. The second effective width $W_{sf}$ as used herein means the largest lateral dimension of the structural feature 320. FIG. 5 indicates that the largest lateral dimension of the structural feature 320 is the diameter. Various dimensions are contemplated for the first effective width $W_{ee}$, the second effective width $W_{sf}$, and the height $H_{ee}$ of the extension element 330. However, the parison 300 is preferably designed such that the second effective width $W_{sf}$ is greater than the first effective width $W_{ee}$ to preserve the structural integrity of the dilation element 130 after blow molding.

Other design configurations for the first effective width $W_{ee}$ and the second effective width $W_{sf}$ are contemplated. For example, the first effective width $W_{ee}$ may be substantially equal to the second effective width $W_{sf}$ such that the extension 330 is characterized by the absence of a necked-down region. Alternatively, the first effective width $W_{ee}$ may be larger than the second effective width $W_{sf}$.

Figure 6:
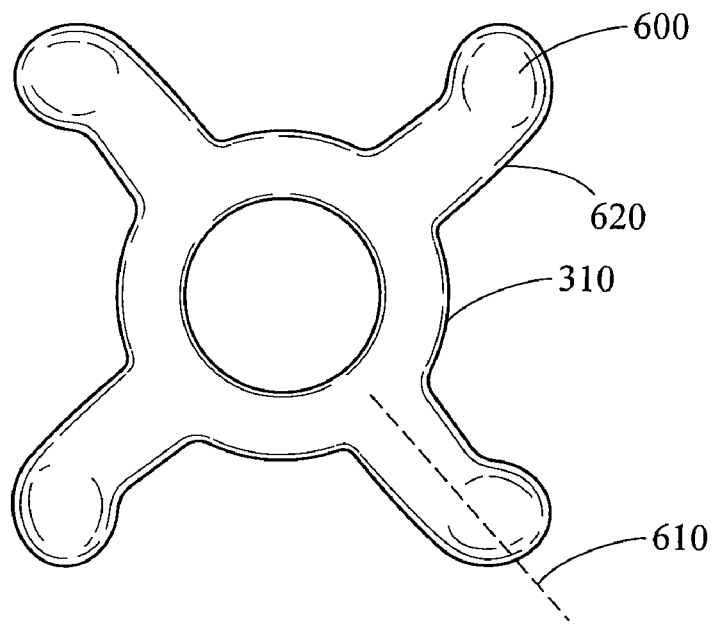
FIGS. 6-8 show possible design configurations of the structural feature and extension element.
Figure 7A:
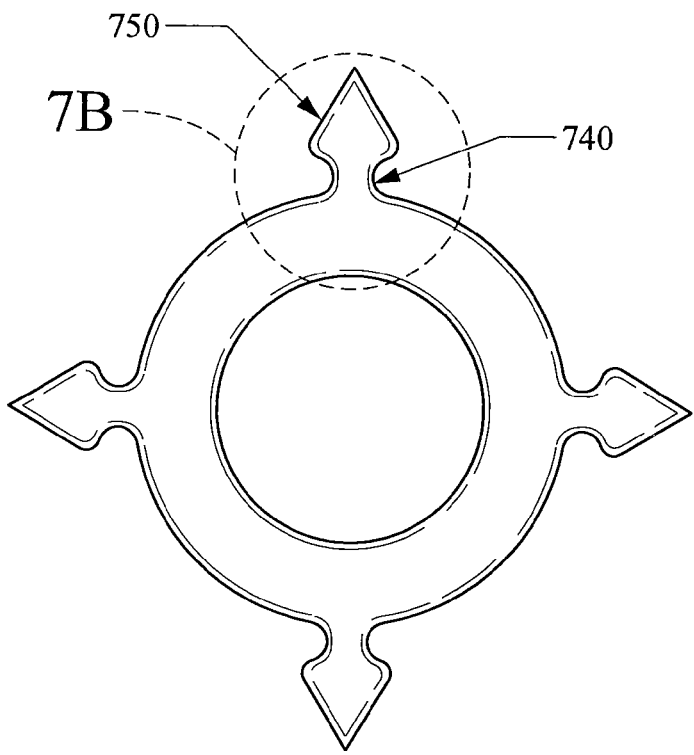
Figure 7B:
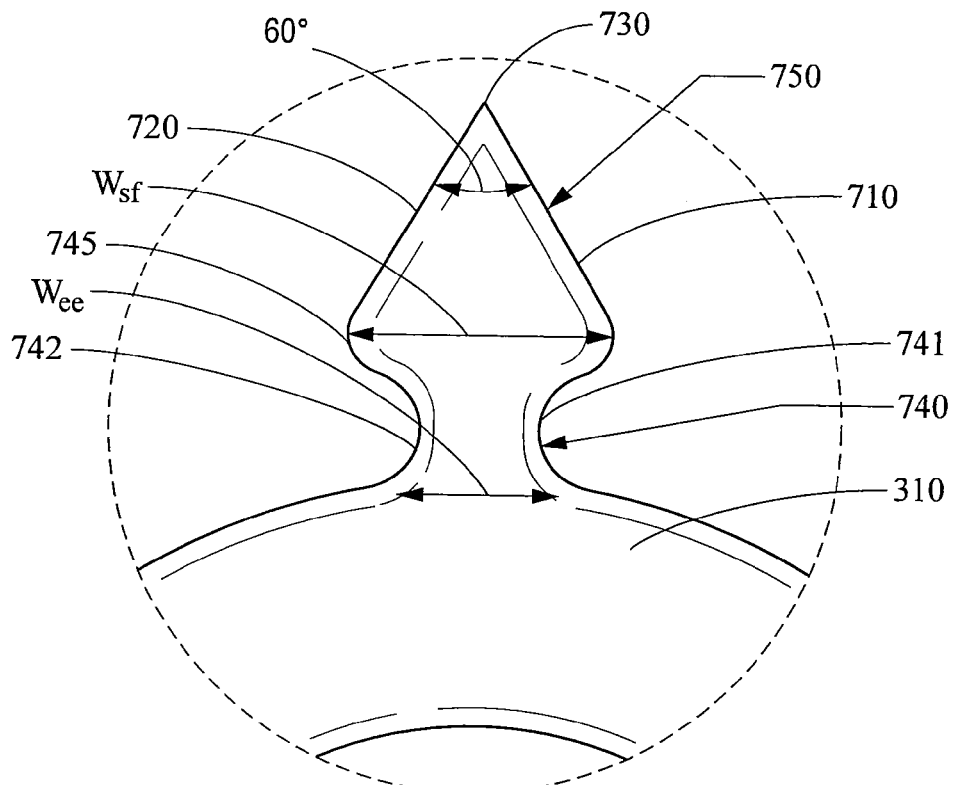
Figure 8:
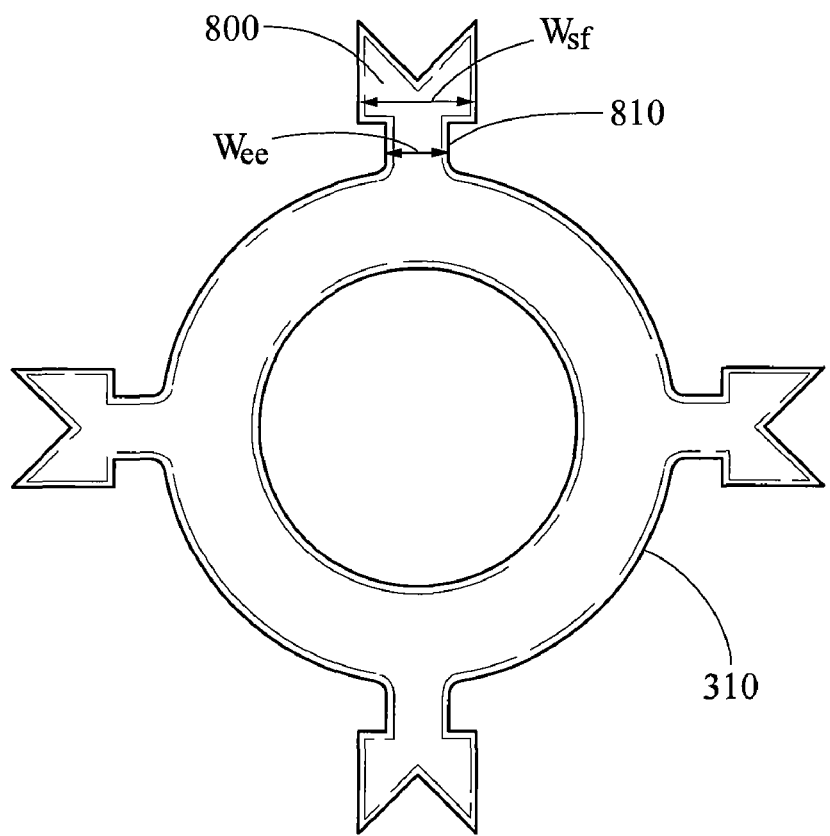

Although FIG. 5 shows that the structural feature 320 is bead-shaped, other shapes for the structural feature and extension element of the parison are contemplated, as shown in FIGS. 6-8. For example, FIG. 6 shows that the structural feature includes a bead-like structure 600 which is asymmetrical about a central radial plane 610 through extension element 620. Each of the bead-like structures 600 includes extension elements 620 which connect the body portion 310 to the asymmetrical bead-like structure 600. The extension elements 620 are shown to be substantially perpendicular to the outer wall 311 of the body portion 310. A radius of curvature may exist at the region at which the extension elements 620 contacts the outer wall 311. The radius of curvature may help to lower the stresses and strains incurred during the radial expansion process of the blow molding process. FIG. 6 shows that the effective width $W_{ee}$ of each of the extension elements 620 is less than the effective width $W_{sf}$ of each of the structural features 600.

FIGS. 7a and 7b show another possible design configuration of the structural feature and extension element about the body portion 310. FIGS. 7a and 7b shows a tapered structural feature 750 having a first edge 720 and a second edge 710. Both edges 710 and 720 taper inwardly towards each other in the radial direction until they terminate at pointed edge 730. Such a tapered structural feature 750 possesses a smaller cross-sectional area at pointed edge 730 which contacts the vessel wall, thereby enabling the force transmitted from the structural feature 730 to the vessel wall to be more focused. The extension element 740 is shown to have curved edges 741 and 742 which connect the body portion 310 to the base 745 of the tapered structural feature 750. FIGS. 7a and 7b show that the effective width $W_{ee}$ of the extension element 740 is less than the effective width $W_{sf}$ of the structural feature 750.

FIG. 8 shows yet another possible design configuration of the structural feature and extension element. FIG. 8 shows a crown-shaped structural feature 800 connected to outer wall 311 of body portion 310 by extension element 810. The extension elements 810 are shown to be substantially perpendicular to the outer wall 311 of the body portion 310. FIG. 8 shows that the effective width $W_{ee}$ of each of the extension elements 810 is less than the effective width $W_{sf}$ of each of the structural features 800.

Various dimensions of the structural feature 320 and extension element 330 (referring for convenience to FIGS. 3-5) are contemplated. For example, the height $H_{ee}$ of the extension element 330 may be greater than the effective width $W_{sf}$ of the structural feature 320. The particular type of design configuration of the structural feature and extension element may be dependent upon numerous factors, including in part the ease of reproducibility of the parison 300 and balloon 150 during manufacturing. Additionally, the height $H_{ee}$ and effective width $W_{ee}$ of extension element 330 should be sufficient to prevent significant absorption of the structural feature 320 into the wall of the parison 300 during blow molding.

Additionally, the parison 300 may be designed to have various configurations of the extension element 330 and structural feature 320. Preferably, the extension element 330 and structural feature 320 are configured longitudinally (FIG.

2) along the outer surface of the parison 300. Alternatively, the extension element 330 and structural feature 320 may spirally extend along the outer surface of the parison 300. Alternatively, the extension element 330 and structural feature 320 may extend only along a finite distance of the parison 300. The parison 300 may also comprise a series of discrete extension elements 330 and structural features 320. The specific configuration of the extension element 330 and structural feature 320 about the parison 300 may be dependent upon numerous factors, including the geometry of the stenosed vessel and the particular application.

Figure 9:
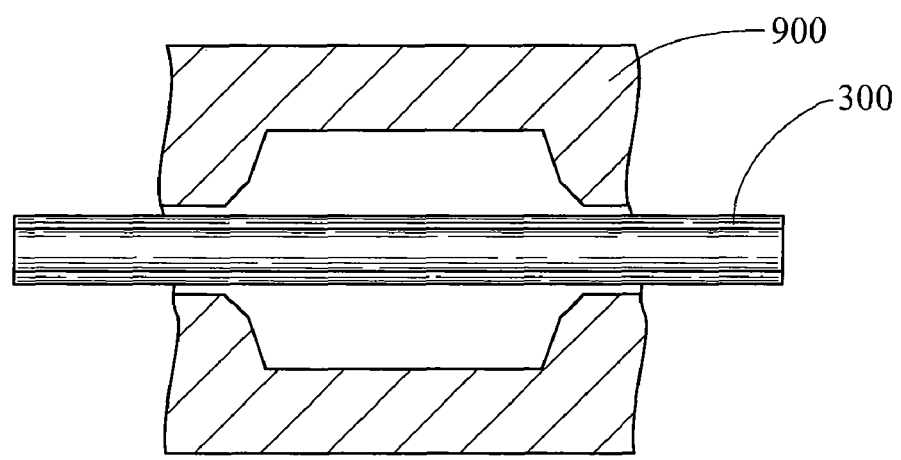
FIG. 9 shows the parison of FIG. 3 placed within a forming mold.
Figure 10:
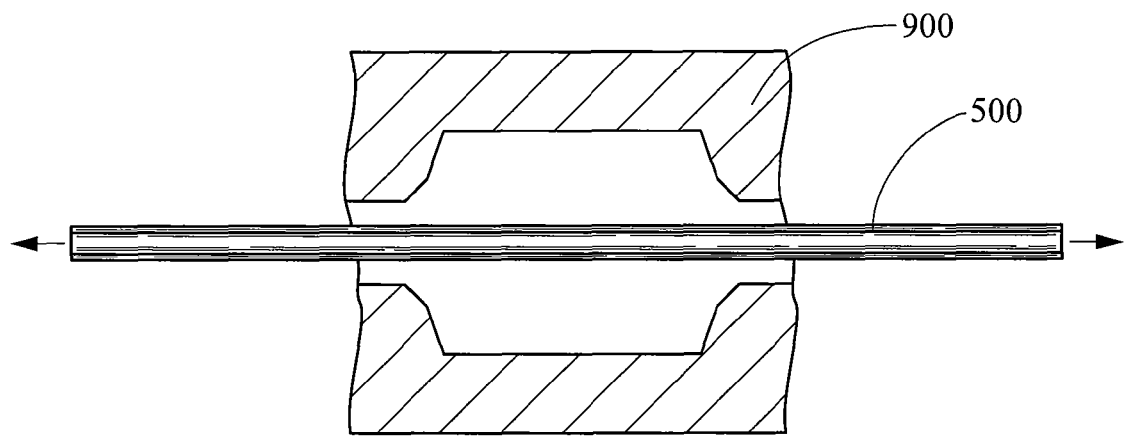
FIG. 10 shows the parison of FIG. 9 longitudinally stretched.
Figure 16:
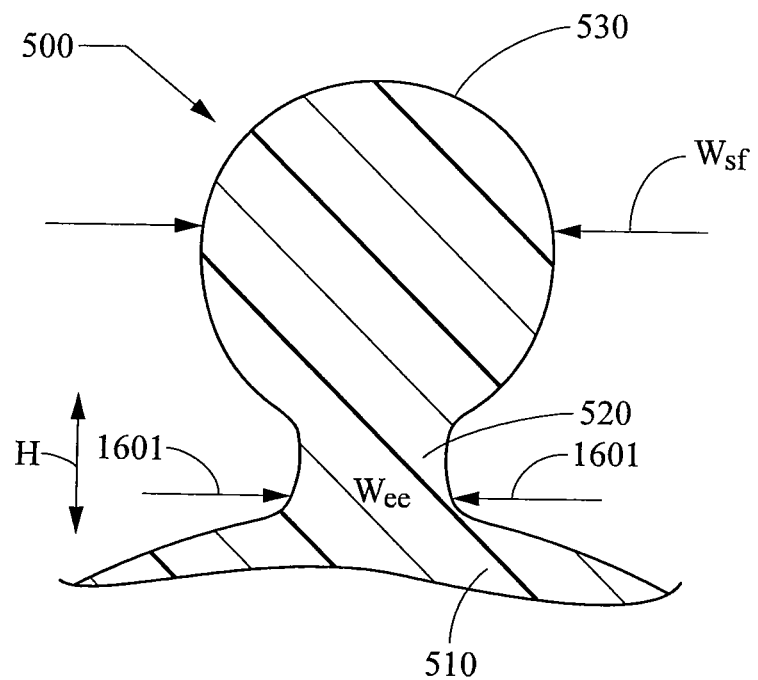
FIG. 16 shows a blown up view of a longitudinally stretched parison.

FIGS. 3-8 represent examples of the type of parisons which may be used for blow molding a balloon into its final shape. The blow molding process forms the final shape and properties of the balloon 150. After selecting the desired shapes and dimensions of the structural feature 320 and extension element 330 (FIG. 3), the parison 300 is placed into a forming mold 900 as shown in FIG. 9. Suitable heat and pressure as known in the art are applied to the parison 300. Thereafter, the parison 500 is stretched in the longitudinal direction as shown in FIG. 10. The longitudinal stretch of the parison 500 decreases the overall cross-sectional area of the parison 300 such that the wall thickness of the parison 300, the effective width $W_{ee}$ of extension element 330, and the effective width $W_{sf}$ of the structural features 320 have decreased dimensions. These overall dimensions of the parison 500 decrease as the parison 500 is being stretched longitudinally. A typical longitudinal stretch of the parison 300 can be from about 2 times to about 4 times the initial inner diameter of the parison 300. FIG. 16 shows the parison 500 after it has been longitudinally stretched. FIG. 16 shows that the effective width $W_{ee}$ of the extension element 520 has decreased relative to the unstretched longitudinal parison 300 of FIG. 5. Accordingly, the height of the extension element 520 has also decreased. Although the effective width $W_{SF}$ of the structural feature 530 has also decreased during the longitudinal stretch of the parison 300, the structural integrity of the feature 530 is shown to remain in tact. In the example shown in FIGS. 5 and 16, the structural feature 530 still retains a bead-like structure.

Figure 11:
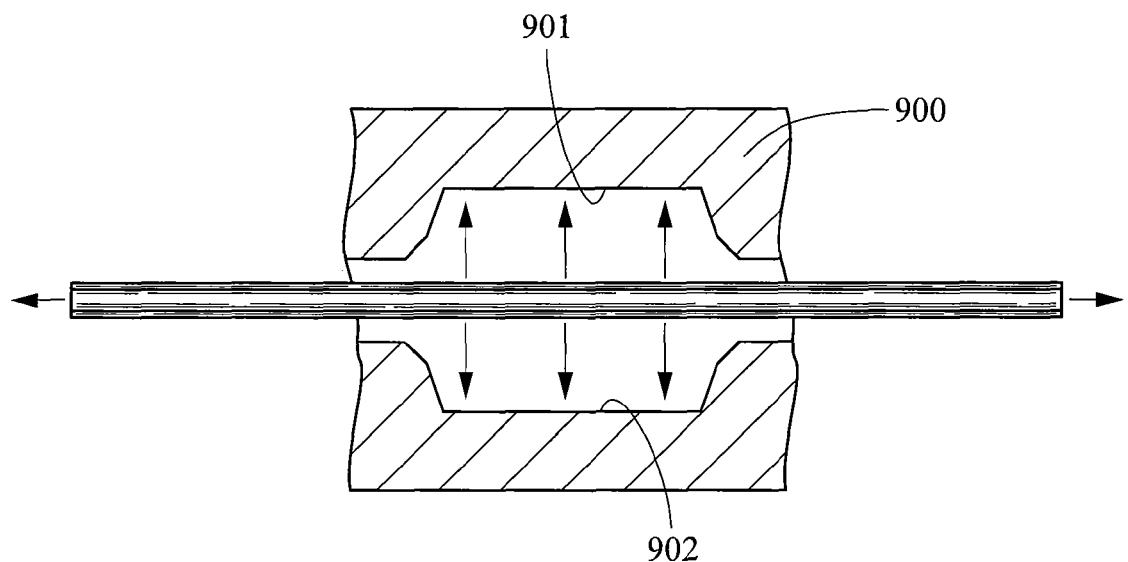
FIG. 11 shows the parison of FIG. 10 about to be radially expanded.

After the parison 300 has been stretched in the longitudinal direction to form the parison 500 of FIG. 5, radial expansion of the parison 500 may occur. FIG. 11 shows that the longitudinally stretched parison 500 radially expands upon applying suitable heat and pressure to the parison 500 as known in the art. The parison 500 radially expands towards the walls 901 and 902 of the mold 900 as indicated by the vertical arrows in FIG. 11. The radial expansion as shown in FIG. 11 gives the longitudinally stretched parison 500 the required radial strength and shape. Radial expansion may be achieved by capping off one of the ends of the parison 500 and then introducing hot pressurized gas or pressurized air into the open uncapped end, thereby causing the parison 500 to expand and conform to the shape of the forming mold 900. The parison 500 may typically expand from about 5 times to about 6 times the initial inner diameter of the parison 300 of FIG. 3. During the radial expansion, the wall thickness of the parison 500 decreases from the radial expansion. The extension element 520 (FIG. 16) undergoes stress-induced plastic deformation during radial expansion and a portion of it becomes part of the wall of the parison 500. The height and effective width of the extension element 520 decreases in the process of becoming part of the wall of the parison 500. However, the shape of the structural feature 530 remains substantially intact during radial expansion of the structural feature 530 (FIG. 16). Preferably, the extension element 530 is designed with sufficient material to undergo stress-induced plastic deformation during the radial expansion without affecting the structural integrity of the structural feature 530.

Figure 12:
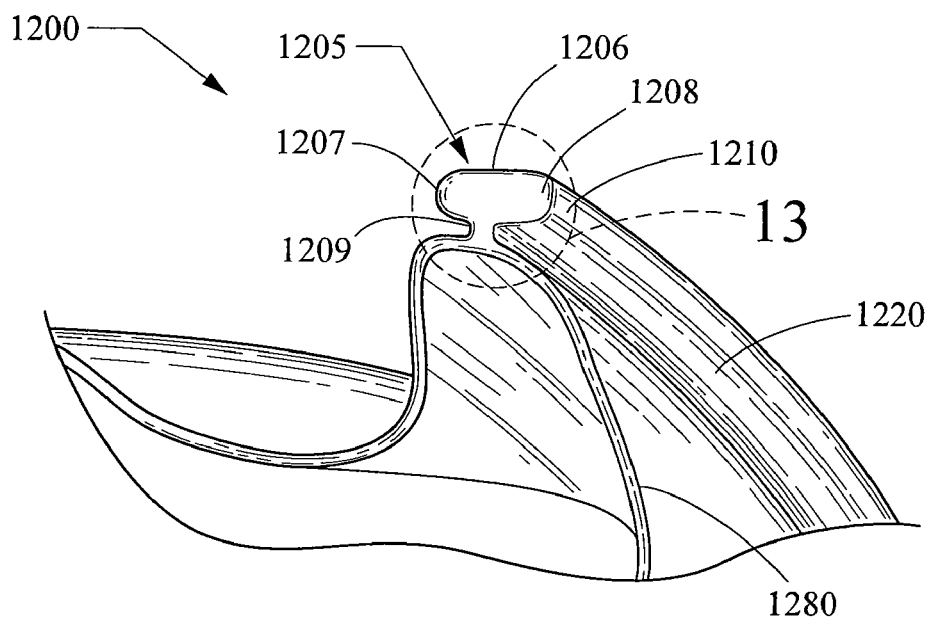
FIGS. 12-13 show the final blow molded balloon structure.
Figure 13:
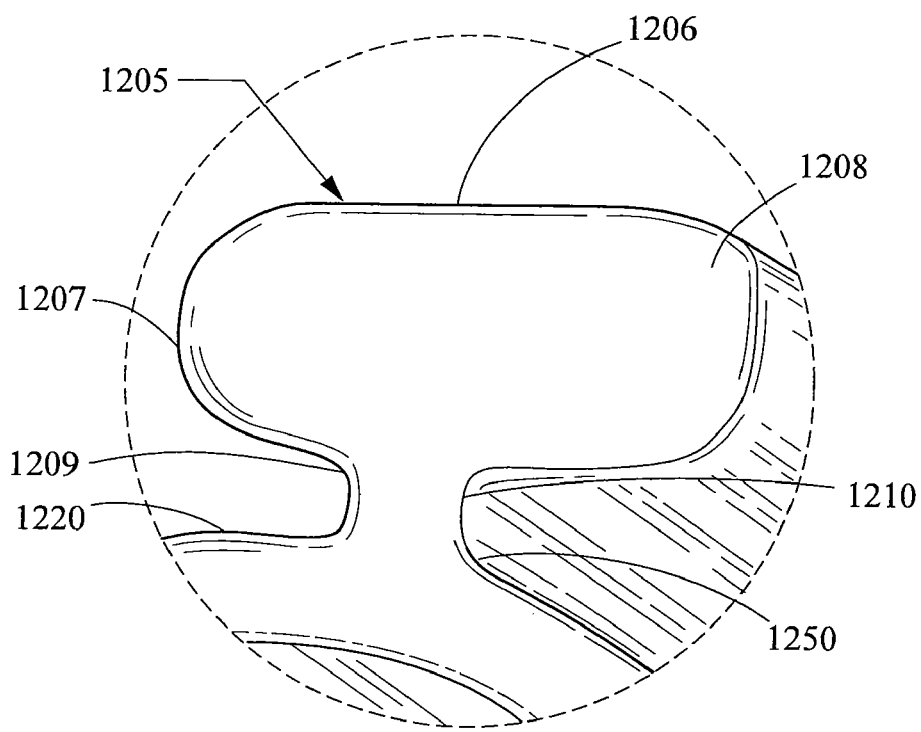
Figure 14:
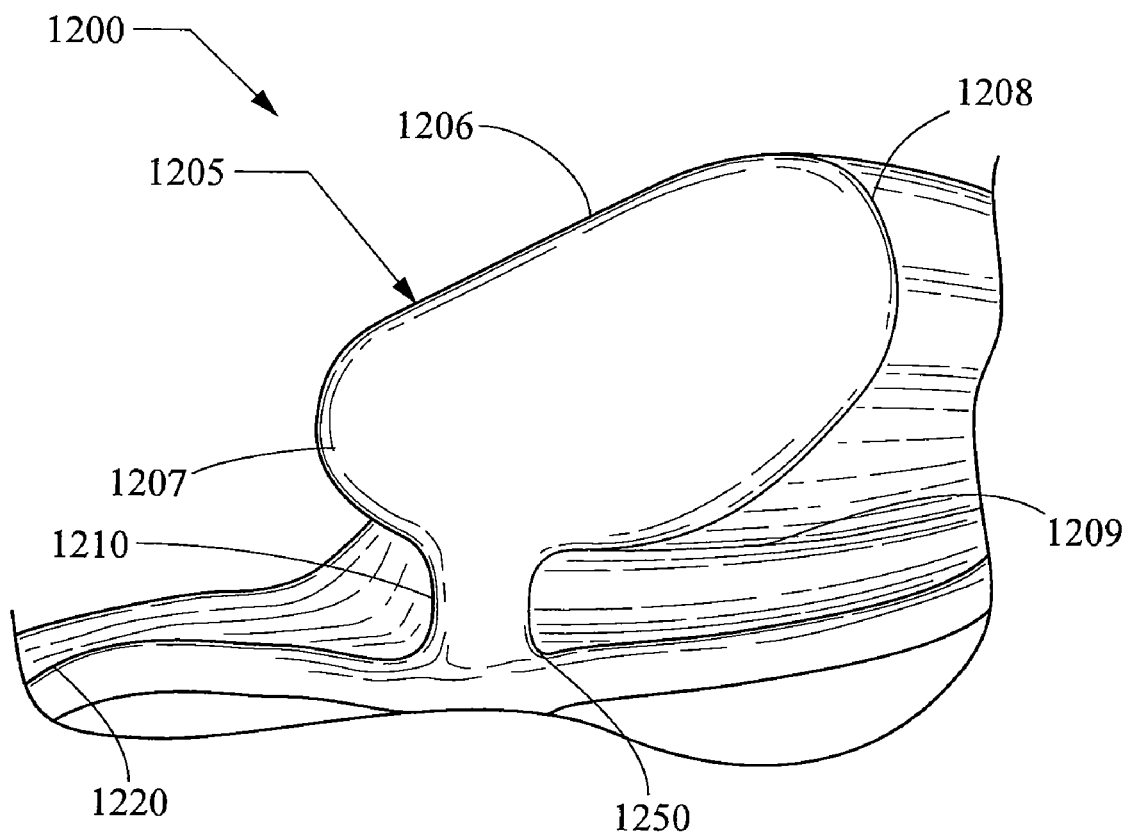
FIG. 14 shows another final blow molded balloon structure.

The resultant balloon after longitudinal stretching and radial expansion is shown in FIGS. 12-14. FIGS. 12 and 13 show an example of a resultant balloon 1200 formed after blow molding of the parison 300 (FIG. 3). FIG. 12 shows a cross sectional view of the final blow molded balloon 1200. Dilation element 1205 extends radially away from the outer surface 1220 of the balloon 1200. The dilation element 1205 includes rounded edges 1207 and 1208 and flattened edges 1206 and 1209. Formation of flattened edge 1206 may occur as the bead-like structural feature 530 (FIG. 12) radially expands and contacts the smooth wall 901 of mold 900. Connector 1210 connects flattened edge 1209 to outer surface 1220 of balloon 1200.

FIG. 13 shows an expanded view of FIG. 12. In particular, FIG. 13 shows that connector 1210 connects flattened edge 1209 to outer surface 1220 of balloon 1200 at an interface region 1250 where the connector 1210 contacts the outer surface 1220 of the balloon 1200. The interface 1250 region is characterized by a wall thickness greater than a wall thickness of a noninterface region, such as that shown at 1280 in FIG. 12. This greater wall thickness at the interface 1250 is attributed to the connector 1210 being absorbed in the wall of the balloon 1200 at the interface region 1250 during blow molding. The extension element 330 of the parison 300 (FIGS. 3 and 4) is preferably designed with suitable height $H_{ee}$ and effective width $W_{ee}$ dimensions such that the resultant connector 1210 possesses sufficient material from which the wall of the balloon 1200 can absorb thereinto without disturbing the shape and structural integrity of the dilation element 1205. FIGS. 12 and 13 show that the effective width of the connector 1210 remains less than the effective width of the dilation element 1205.

Although the dilation element 1205 is shown radially oriented with respect to the outer surface 1220 of the balloon 1200, numerous other configurations of the resultant dilation element 1205 are contemplated. For example, the dilation element 1205 may be inclined relative the outer surface 1220 of the balloon 1200, as shown in FIG. 14. Such a configuration may be formed during radial expansion (FIG. 11), in which the structural feature 530 (FIG. 16) becomes inclined after contacting the wall 901 of mold 900 at an angle.

Figure 15:
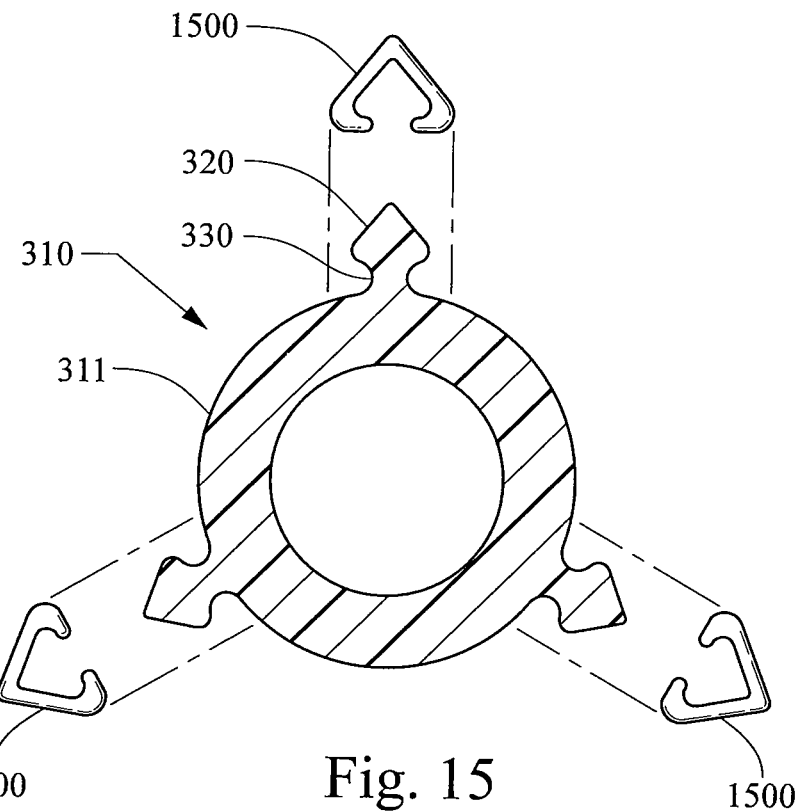
FIG. 15 shows a protective jacket which may be placed over a structural feature of the parison before blow molding the parison.

Flattened edge 1206 of dilation element 1205 has greater surface area than the unflattened edge of corresponding structural feature 320 (FIG. 3), which is shown to have a bead-like shape. The edge 1206 may be maintained in a shape having smaller surface area to enhance the focusing of the pressure transmitted from edge 1206 to a stenosed vessel wall. Various techniques may be utilized to prevent edge 1206 of structural feature 320 from flattening when contacting an inner surface of the mold 900. For example, FIG. 15 shows a jacket 1500 which may be placed over the structural feature 320 of the parison 300 before blow molding the parison 300. The jacket 1500 shields the structural feature 320 from the inner surface of the wall 901 of the mold 900 during radial expansion of parison 300 within the mold 900, thereby maintaining the shape of the structural feature 320. The jacket 1500 may be a pre-formed molding that is formed from a material that has a higher melt temperature than the temperature used during blow molding. Examples of suitable materials for the jacket 1500 include PEEK, PTFE, and other relatively high-melt temperature materials. Because the jacket 1500 has a higher melt temperature than the temperatures utilized during blow molding, the shape of the jacket 1500 may be maintained. The material of the jacket 1500 may also be sufficiently heat resistant (e.g., KEVLAR®) to prevent heat transfer from the exterior of the mold into the interior region of the mold. As a result of the heat resistant properties of the jacket 1500 material, the structural feature 320 may be prevented from being heated to its melt temperature.

Figure 17:
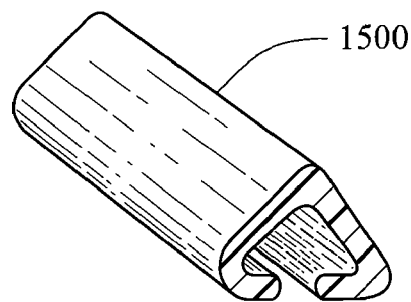
FIG. 17 shows a perspective view of the protective jacket of FIG. 15.

A perspective view of the jacket 1500 is shown in FIG. 17. The longitudinal length of the jacket 1500 may be sufficient to span the entire length of each of the structural features 320 of the parison 300. Screws, clips, adhesives or other joining methods known to one of ordinary skill in the art may be used to secure the jacket 1500 around its respective structural feature 320.

Figure 18:
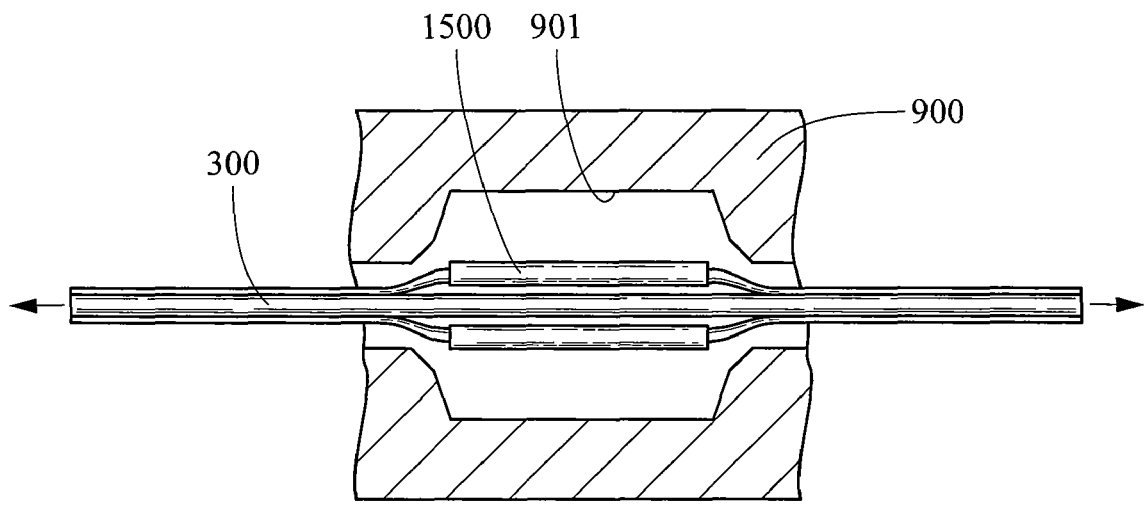
FIG. 18 shows a longitudinal cross-sectional view of the jacket disposed over the parison.

Alternatively, the jacket 1500 may be designed to snap fit over its respective structural feature 320. A snap fitted jacket 1500 may flex like a spring, usually over a designed-in interference, and return to its original position to create the desired snap assembly between two or more parts. The snap-fit assembly of the jacket 1500 and its structural feature 320 may be designed to have adequate holding power without exceeding the elastic or fatigue limits of either material. FIG. 18 shows a longitudinal cross-sectional view of a single jacket 1500 disposed over the region of the parison 300 containing structural features 320 within mold 900. As the jacket 1500 and parison 300 radially expand during blow molding, as indicated by the arrows in FIG. 18, the jacket 1500 protects the structural features 320 from flattening upon contacting wall 901 of mold 900. After the blow molding is completed, the snap-fitted jacket 1500 may be released from its structural feature 320 with an appropriate tool. The snap-fitted jacket 1500 may be designed for easy release and re-assembly over multiple blow-molding cycles.

As shown in FIG. 15, multiple jackets 1500 may be used to cover all of the features. Alternatively, one or more jackets 1500 may be used to cover less than all of the features.

Other means may be utilized to prevent edge 1206 of structural feature 320 from flattening when contacting an inner surface of the mold 900 during blow molding of the parison 300. For example, a second mold may be used to reshape the dilation elements 130 (FIGS. 1, 3, 4) into the originally shaped structural features 320 as well as realign the dilation elements 130 along the longitudinal direction of the balloon 150 (FIG. 1). The second mold may possess multiple grooves into which each of the dilation elements 130 insert thereinto. The entire parison 300 may be inserted into the second mold. Alternatively, only structural features 320 may be inserted into the second mold, and the body portion of the parison 300 remains outside of the second mold. Alternatively, the original mold used in the blow molding process may contain multiple grooves into which the structural features 530 can expand. The structural features 530 conform to the shape of the grooves to form the resultant dilation elements 1205. Other means as known in the art for preserving the desired bead shape are contemplated.

Preferably, the resultant balloon 150 that is formed after the blow molding process described in FIGS. 9-11 comprises dilation elements 130 (FIGS. 1, 3, 4) and connector 120. Because the extension elements 330 (FIG. 3) undergoes stress-induced plastic deformation during the blow molding process, the structural integrity of the resultant dilation elements 130 is maintained such that they do not become part of the wall of the body portion 310. As a result, upon inflation of the balloon 150, the dilation elements 130 remain structurally intact to focus the force at their respective points of contact with a stenosed vessel wall. Because FIGS. 1, 3, and 4 show that the dilation elements 130 are integrally part of the parison 300 (i.e., raw balloon tubing), secondary processes are not required for attachment to the outer surface 140 of the balloon 150.

The resultant balloon 150 preferably comprises dilation elements 130 which are circular-shaped, as shown in FIGS. 3 and 4. Other shapes are contemplated. For example, a dilation element 1320 which is offset from a central radial plane through the connector is another possible design.

Figure 19:
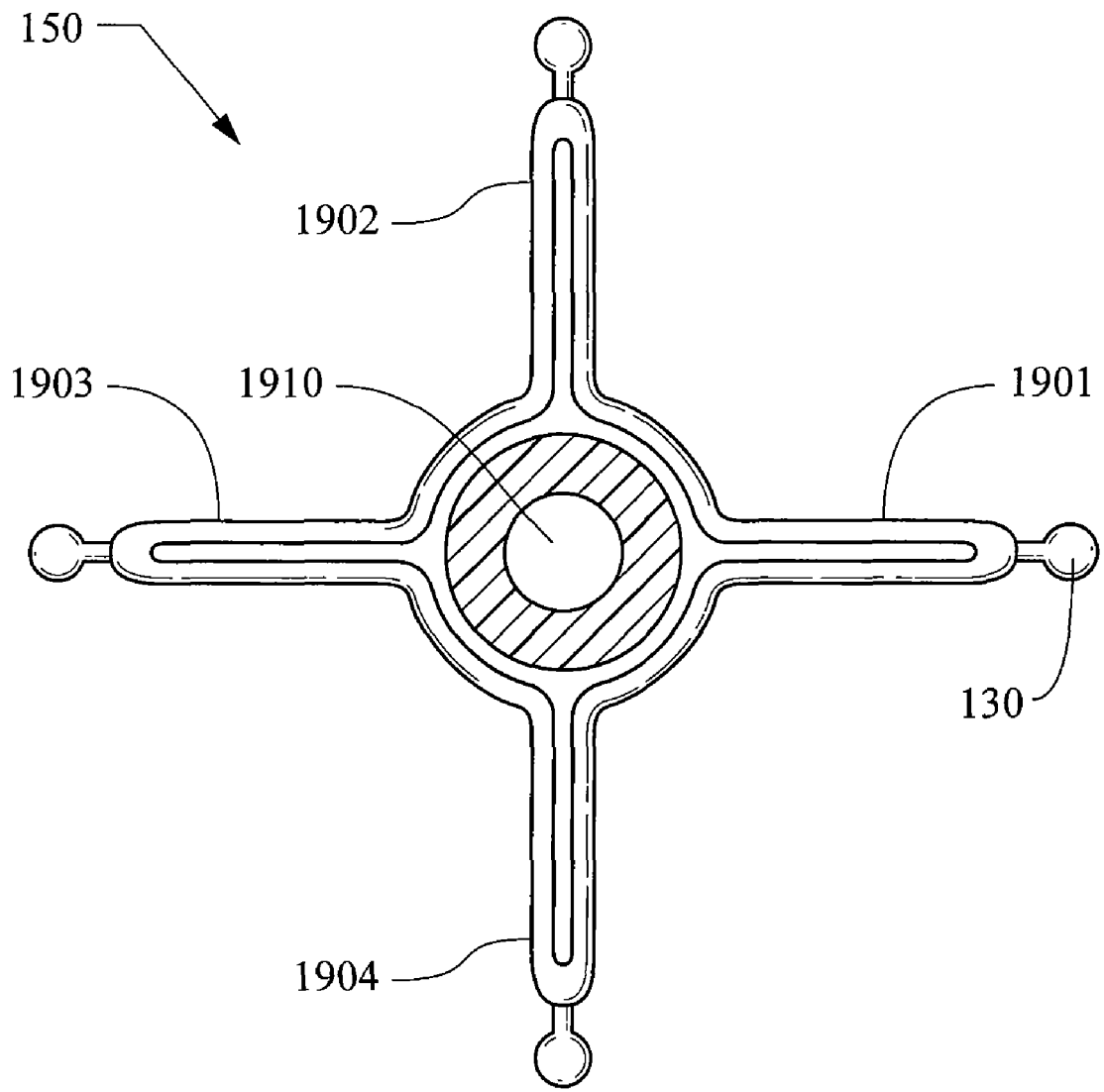
FIG. 19 shows the balloon in a deflated state having a folded arrangement with the dilation element and connector disposed along the top of the folds.

The resultant balloon 150 is preferably folded into a pleated configuration of small diameter for delivery to a target stenosed vessel site. The pleats are initially formed during delivery of the balloon 150 and may be reformed upon deflating the balloon 150 from the inflated state. FIG. 19 shows the balloon 150 in a deflated state having a pleated arrangement with the dilation element 130 and connector 120 disposed along the top of each of the pleats 1901, 1902, 1903, and 1904. Upon delivery and deflation from the inflated state, the balloon 150 transforms into the pleated arrangement. Four pleats 1901, 1902, 1903, and 1904 are shown positioned circumferentially about a central axis of the balloon 150. Less than four pleats or greater than four pleats may be utilized depending, in part, upon the profile of the balloon 150 required for a particular application. The pleats 1901, 1902, 1903, and 1904 may be wrapped about a central axis of the balloon 150 to form the pleated arrangement, thereby creating a sufficiently low profile of the balloon 150 during delivery to and removal from the target site.

The dilation elements 130 and their respective connectors 120 are shown preferably extending from the top of the pleats 1901, 1902, 1903, and 1904. The presence of the dilation elements 130 and their respective connectors 120 disposed along the top of the pleats 1901-1904 may facilitate the ability of the inflated balloon 150 to refold into the pleated configuration of FIG. 19. When the balloon 150 is deflated, the balloon 150 material between pleats 1901-1904 may have a higher tendency to collapse than the pleated region of the balloon 150 material. In other words, the balloon 150 material between the pleats 1901-1904 has less resistance to collapsing into the pleated arrangement than the pleated region. The pleated region has a greater wall thickness and therefore possesses relatively greater rigidity as a result of at least a portion of the extension element 330 of the parison 300 absorbing into the wall during radial expansion of the parison 300 within the mold 900.

Alternatively, the pleats 1901, 1902, 1903, and 1904 may be configured such that the dilation elements 130 are disposed between adjacent pleats 1901, 1902, 1903, and 1904.

The ability to reform the pleated configuration may prevent the undesirable phenomenon known in the art as "winging" from occurring. Winging refers to flattening of the balloon 150 into a wing-like structure characterized by an absence of folds along the balloon 150. Because there are no folds, the profile of the balloon 150 may become relatively wide such that removal and reentry of the balloon 150 within an outer sheath potentially becomes difficult. Thus, the pleats 1901-1904 may substantially eliminate the winging problem.

The balloon 150 may be formed from any suitable polymeric material known to those of ordinary skill in the art, including polyethylene terephthalate (PET) and nylon. In one preferred embodiment, the material is Grilamid® L25, which is a specific nylon-12 material known in the art. Alternatively, the balloon 150 may be formed from a first polymeric material and the protuberance 110 may be formed from a second polymeric material.

In one particular embodiment, the balloon 150 and protuberance 110 may be coextruded from two different materials. The balloon 150 may be extruded from a conventional first polymeric material (e.g., nylon), the dilation element 130 may be extruded from a second polymeric material more rigid than the first polymeric material, and the connector 120 may be extruded from a blend of the first and the second polymeric materials. A transition point from the first polymeric material to the second polymeric material preferably occurs along the connector 120. In particular, it is preferable that a lower portion of the connector 120 (i.e., from the predetermined transition point along the connector 120 downwards to the interface of the connector 120 and the outer surface 140 of the balloon 150) may be formed from the same first polymeric material as the outer surface 140 of the balloon 150 to enable this lower portion of the connector 120 to become absorbed into the wall of the balloon 150 during the blow molding process. The first polymeric material may be relatively softer and more compliant than the second polymeric material, thereby enabling longitudinal and radial stretching during blow molding. The lower portion of the connector 120 may be adequately sized such that there is a sufficient amount of first polymeric material that absorbs into the wall of the balloon 150 without substantial absorption of the upper portion of the connector 120 (i.e., from the predetermined transition point along the connector 120 upwards to the dilation element 130) into the wall of the balloon 150. The upper portion of the connector 120 is connected to the dilation element 130. The dilation element 130 contacts the stenosed vessel wall.

Figure 20:
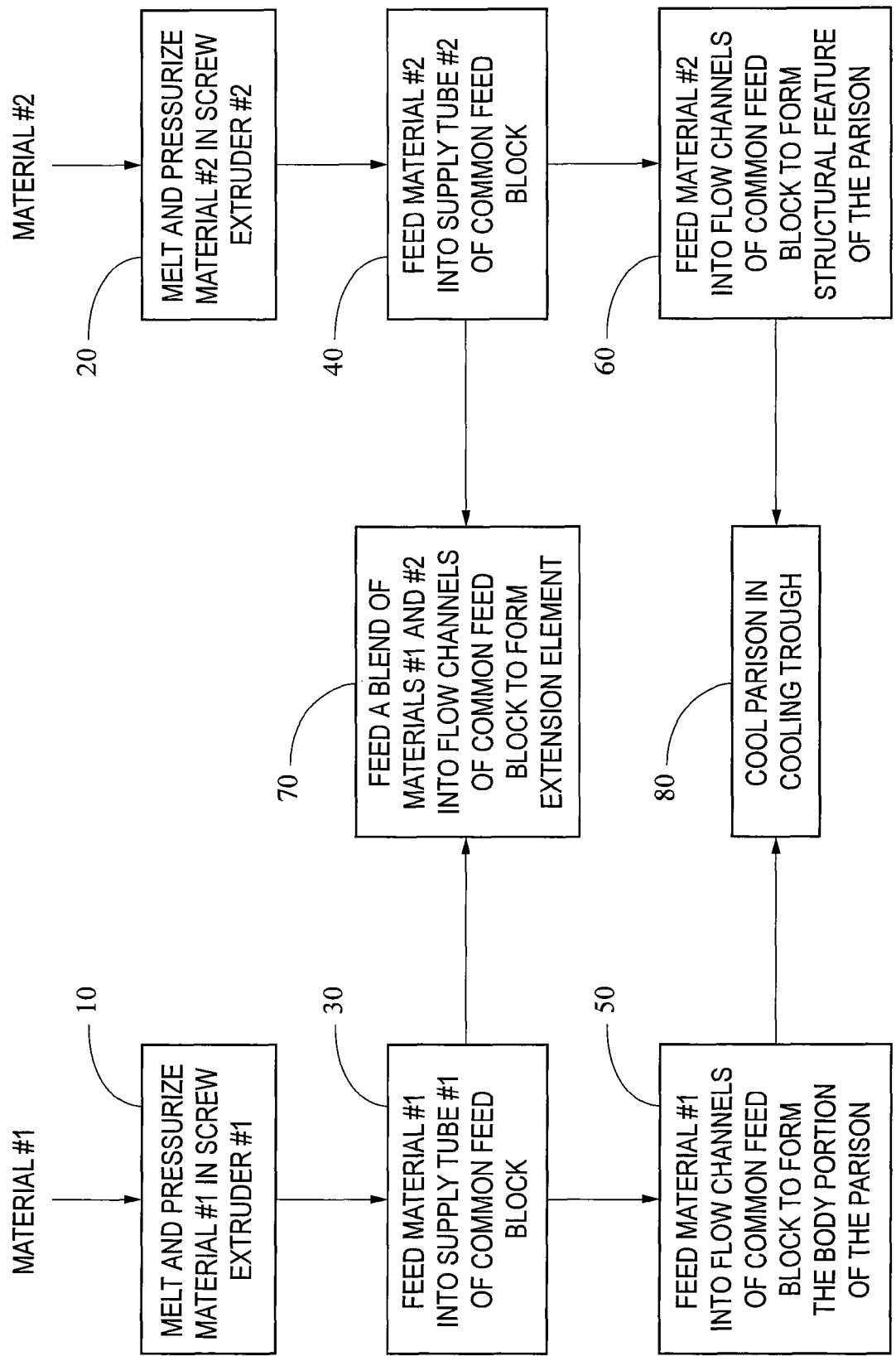
FIG. 20 shows a block diagram of a coextrusion process for forming a balloon from a first polymeric material and an extension element from a blend of the first and a second polymeric material, and a structural feature from the second polymeric material.

The blending of a first polymeric and a second polymeric material may be achieved by several different types of coextrusion processes. One particular screw extrusion process is shown in the block diagram of FIG. 20. FIG. 20 shows that the relatively softer first polymeric material #1 is extruded in screw extruder #1 and the relatively more rigid second polymeric material #2 is extruded in screw extruder #2, as shown in respective steps 10 and 20. Each of the materials is melted and pressurized in their respective extruders #1 and #2 (respective steps 10 and 20). Each screw extruder #1 and #2 provides discrete flow channels through which materials #1 and #2 flow therewithin. Screw extruder #1 may feed into a supply tube #1 within a common feed block (step 30), and screw extruder #2 may feed into a supply tube #2 within the common feed block (step 40). Each supply tube may thereafter branch off into multiple flow channels located internally of the feed block. The flow channels enable material #1 to enter specific portions of the parison mold in step 50 to form the body portion 310 of the parison 300 (FIG. 3). Another group of flow channels enable material #2 to feed into that portion of the parison mold which forms the structural feature 320 of the parison 300 (step 60). Yet another group of flow channels converge into a single flow channel and thereafter feed into that portion of the parison mold along the extension element 330 of the parison 300, so as to form extension element 330 and also allow mixing of material #1 and material #2 at a transition point located along the extension element 330 of the parison 300 (step 70). The feed block may be designed such that mixing of material #1 and #2 may occur simultaneously with the shaping of the extension element 330.

Materials #1 and #2 are preferably selected such that there is compatibility in at least two ways. First, selection of suitable materials #1 and #2 may require that both materials #1 and #2 have a common processing temperature range. In other words, the materials #1 and #2 have a common temperature range such that both materials #1 and #2 can be processed within the common temperature range without thermal degradation of one of the materials. Second, selection of suitable materials #1 and #2 is such that they have an affinity for each other so when combined into the flow channels of the feed block, a natural chemical bond is formed between the materials which assures that materials #1 and #2 do not separate upon incurring a load during subsequent blow molding of the parison 300 into the balloon 150. A modification step to one or both of the materials #1 or #2 may be carried out prior to step 70 to functionalize the materials #1 or #2 so that they are chemically compatible with each other, thereby forming a chemical bond.

The extrudate from steps 50 and 60 and the coextrudate from step 70 are cooled in cooling troughs, as shown in step 80. The cooling troughs cool material and solidify the extrudate into the desired shape of the parison 300. The net result is a coextruded parison in which the body portion 310 and a lower portion of the extension element 320 are formed from softer, compliant material #1 and an upper portion of the extension element 330 and structural feature 320 is formed from relatively more rigid, less compliant material #2. Other means for blending two different materials to form a monolithic (i.e., unitary) extrudate parison structure as known to one of ordinary skill in the art are also contemplated.

In an alternative embodiment, the cylindrical portion of the parison and the extension element-structure feature may not be a monolithic structure but rather may be separately extruded structures. Furthermore, the cylindrical portion of the parison may be formed from a first polymeric material and the extension element-structure feature may be formed from a blend of the first and the second polymeric materials, as described above. The cylindrical portion of the parison and the extension element-structure feature may be separately extruded and subsequently attached to each other. Various means may be utilized for connecting the lower portion or base of the extension element to the cylindrical portion of the parison, including a thermal bond. One preferred type of thermal bond could involve laser welding the base of the extension element to the cylindrical portion of the parison. The laser weld enables pinpointing high heat in a localized area (i.e., at the interface of the connector and the outer surface of the balloon) without adversely impacting the balance of the cylindrical portion of the parison and the structural feature. Alternatively, a chemical bond such as an adhesive bond may be used to attach the base of the extension element to the cylindrical portion of the parison. The particular connecting means may be dependent upon the materials of the parison, extension element, and structural feature.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A method of forming a balloon, comprising the steps of:
   (a) providing a blow mold parison comprising:
      a substantially cylindrical body portion, the body portion comprising an outer wall and an inner wall, the body portion further comprising an aperture extending along a central axis of the body portion;
      an extension element projecting away from the outer wall of the body portion, the extension element being integrally molded to the body portion, the extension element comprising a first height and a first effective width; and
      a structural feature projecting from the outer wall of the body portion, the structural feature being integrally molded to the extension element, the structural feature comprising a second effective width greater than the first effective width of the extension element;
(b) inserting the blow parison into a forming mold;
(c) applying a predetermined amount of heat and pressure to the parison;
(d) stretching the parison in a longitudinal direction; and
(e) expanding the parison in a radial direction, wherein the extension element undergoes stress-induced plastic deformation developed during the radial expansion to maintain structural integrity of the structural feature.

2. The method of claim 1, further comprising the step of placing a jacket over the structural feature prior to the longitudinal stretching and the radial expansion of the parison.

3. The method of claim 1, wherein step (e) further comprises the extension element preventing substantial expansion of the structural feature during the radial expansion.

4. The method of claim 1, wherein step (a) further comprises extruding the body portion of the parison and a lower portion of the extension element from a first material and extruding an upper portion of the extension element and structural feature from a second material less compliant than the first material.

5. The method of claim 1, wherein the steps of longitudinal stretching and radial expanding the parison transforms the extension element into a connector and transforms the structural feature into a dilation element.

6. The method of claim 1, further comprising the step of decreasing the second effective width of the structural feature to a third effective width.

7. The method of claim 6, further comprising the step of decreasing the first effective width of the extension element to a fourth effective width, the fourth effective width being less than the third effective width.

* * * * *